United States Patent [19]

Thompson

[11] 4,270,416
[45] Jun. 2, 1981

[54] SCALPEL BLADE EXTRACTOR

[75] Inventor: David K. Thompson, London, England

[73] Assignee: Jermed Limited, St. Helier, Channel Islands

[21] Appl. No.: 31,807

[22] Filed: Apr. 20, 1979

[30] Foreign Application Priority Data

Apr. 21, 1978 [GB] United Kingdom ............... 15886/78

[51] Int. Cl.³ .......................... B25B 27/14; B65F 7/00
[52] U.S. Cl. ...................................... 81/3 R; 30/339; 206/359
[58] Field of Search ..................... 30/339, 123; 29/267, 29/278; 81/3 R; 206/355, 359, 370

[56] References Cited

U.S. PATENT DOCUMENTS

| | | | |
|---|---|---|---|
| 3,172,316 | 3/1965 | Grieshaber | 81/3 R |
| 3,244,317 | 4/1966 | Raybin | 206/355 X |
| 3,262,205 | 7/1966 | Arden | 30/339 |
| 3,373,491 | 3/1968 | Montelius | 30/339 |
| 4,106,620 | 8/1978 | Brimmer | 206/359 X |
| 4,120,397 | 10/1978 | Neumann | 206/370 |
| 4,121,329 | 10/1978 | Sugiyama | 81/3 R |
| 4,168,777 | 9/1979 | Gaskell | 206/359 |
| 4,180,162 | 12/1979 | Magney | 206/359 X |

Primary Examiner—Jimmy C. Peters

Attorney, Agent, or Firm—Wender, Murase & White

[57] ABSTRACT

A hand held device is provided which permits safe removal of used blades from scalpels or the like in which a slotted blade is received in opposed lateral grooves in a thin elongate tang with a proximal region of the blade located behind the tang in a cut-away laterally convergent region intermediate the tang and the handle. The device includes a base wall over whose surface the scalpel is advanced and having laterally opposed protuberant regions over which the blade slides. A slot between the protuberant regions which receives the tang but not the blade. A fully inserted position of the scalpel is defined by abutment between the proximal edges of the protuberant regions and said convergent region. A rear wall is supported behind the slot with its lower edge spaced from the base wall to allow the scalpel and blade to be inserted therebetween and to allow a fully inserted scalpel to be pivoted about the lower edge to a tilted orientation in which the proximal end of the blade is levered away from the intermediate region clear of the tang and is retained by interference with the rear wall during removal of the scalpel handle in the tilted orientation. Guide surfaces proximally of the slot direct the scalpel blade or handle into the slot.

5 Claims, 17 Drawing Figures

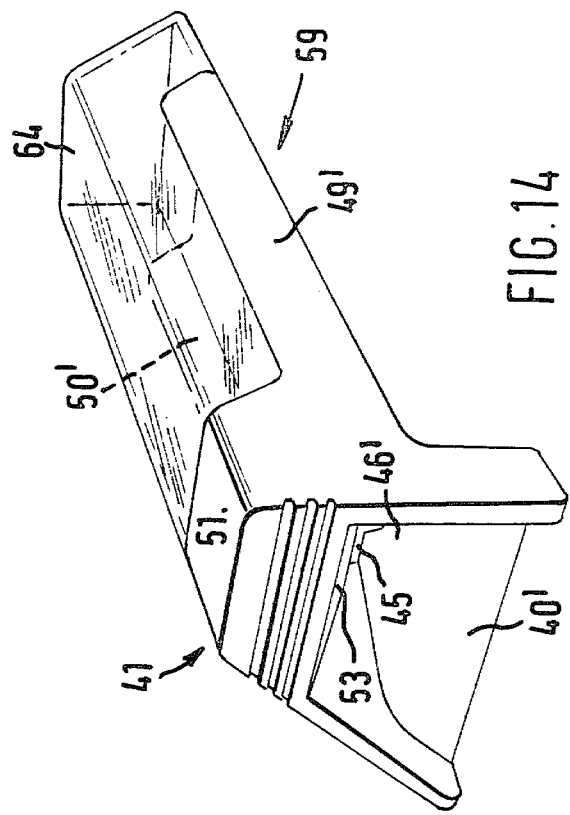
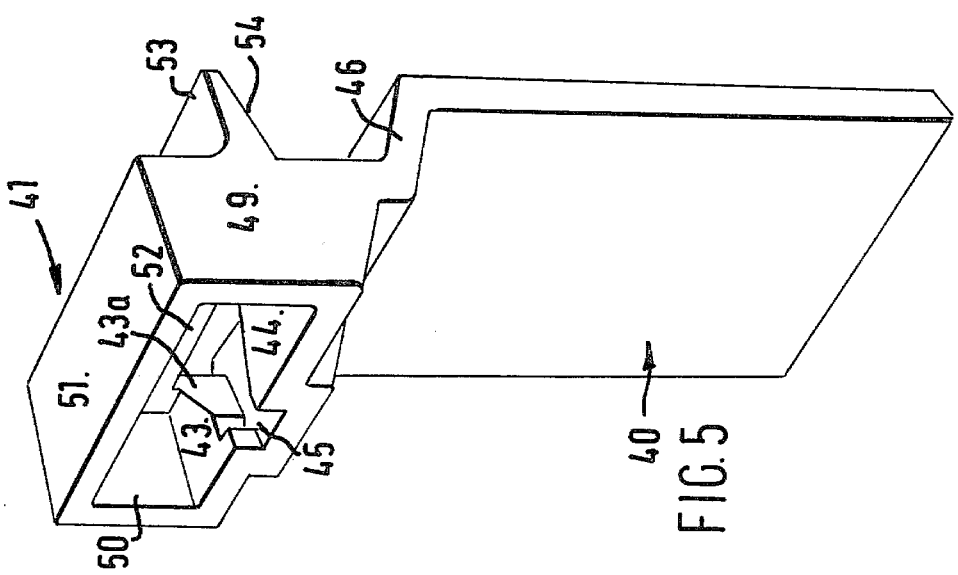

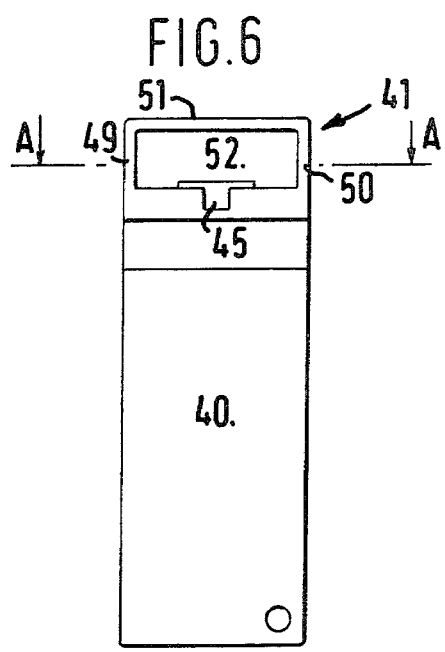
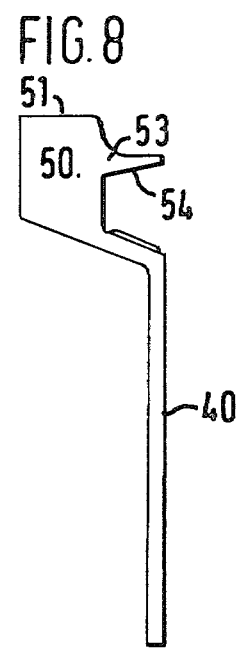
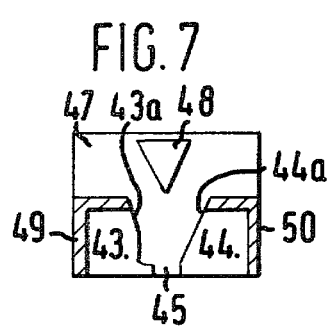
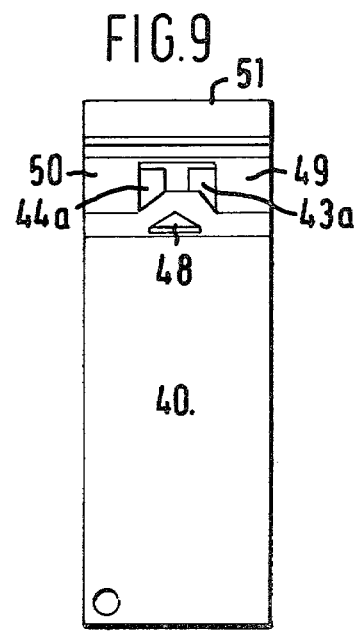

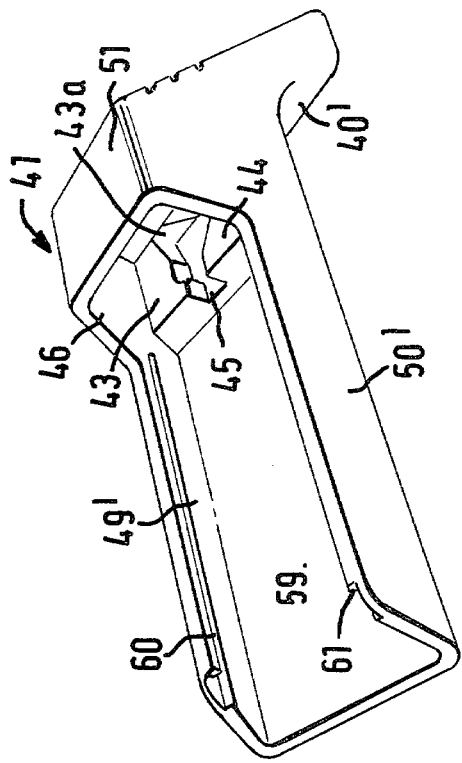
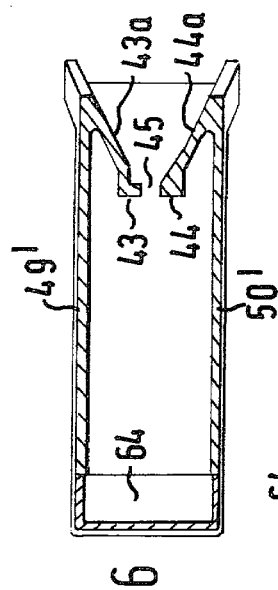
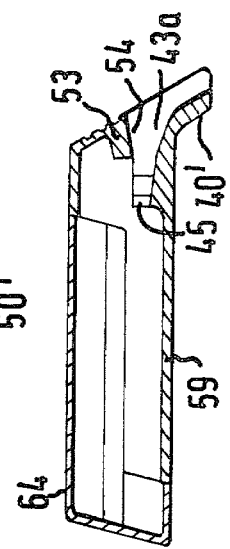
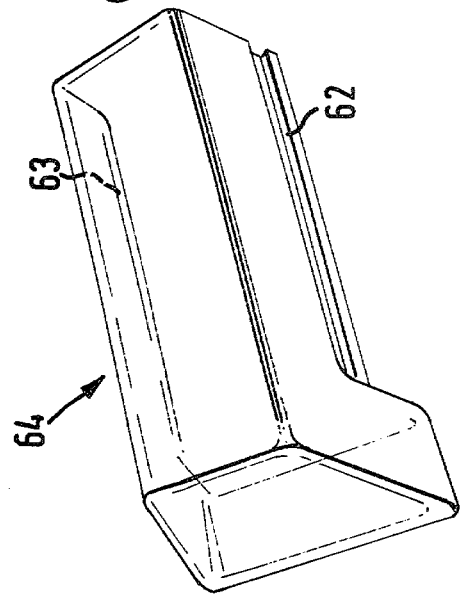
FIG.15   FIG.16   FIG.17

SCALPEL BLADE EXTRACTOR

BACKGROUND OF THE INVENTION

The present invention relates to a device for removing detachable blades from the handles of scapels or the like.

Removal of blades from scalpels has hitherto been carried out manually and is dangerous because there is a risk of a person involved cutting himself or herself. A need exists for a simple and inexpensive device by means of which this job can be done rapidly and safely.

SUMMARY OF THE INVENTION

Broadly stated, the invention provides a device for removing a detachable blade from a scalpel or the like in which a slotted blade is received in opposed lateral grooves in a thin elongate tang with a proximal region of the blade located behind the tang in a cut-away laterally convergent region intermediate the tang and the handle, the device including a base wall over whose surface the scalpel is advanced and having laterally opposed protuberant regions over which the blade slides and a slot between the protuberant regions which can receive the tang but not the blade, a fully inserted position of the scalpel being defined by abutment between the proximal edges of the protuberant regions and said convergent region, a rear wall supported behind the slot with its lower edge spaced from the base wall to allow the scalpel and blade to be inserted therebetween and to allow a fully inserted scalpel to be pivoted about the lower edge to a tilted orientation in which the proximal end of the blade is levered away from the intermediate region clear of the tang and is retained by interference with the rear wall during removal of the scalpel handle in the titled orientation, and guide surfaces proximally of the slot for directing the scalpel blade or handle into the slot.

Further and additional features of the invention will be apparent from the description, claims and drawings.

BRIEF DESCRIPTION OF THE DRAWINGS

The invention will be further described, by way of example only, with reference to the accompanying drawings, in which like numerals denote like parts and;

FIG. 5 is a front perspective view of a first embodiment of a blade extractor;

FIG. 6 is a front view of the blade extractor shown in FIG. 5;

FIG. 7 is a horizontal section of the aforesaid blade extractor taken along the line A—A of FIG. 6;

FIG. 8 is a side view of the blade extractor shown in FIG. 5;

FIG. 9 is a rear view of the blade extractor shown in FIG. 5;

FIG. 14 is an oblique view from the blade insertion end of a second embodiment of a blade extractor;

FIG. 15 is an oblique view of the blade extractor of FIG. 14 from the opposite end and with the cover removed; and FIGS. 16 and 17 are views of the blade extractor of FIG. 14 in horizontal and vertical section respectively.

CONSTRUCTION OF SCALPELS HAVING DETACHABLE BLADES

Figure 1:
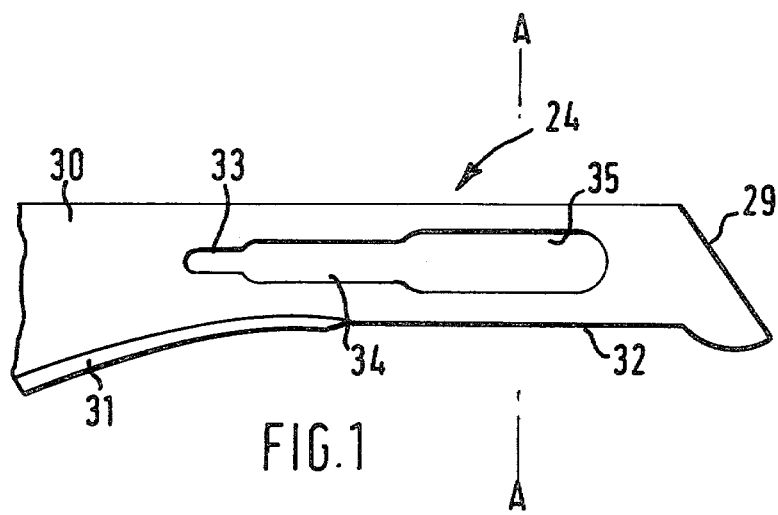
FIG. 1 is a plan view of the proximal end of a disposable scalpel blade.
Figures 2, 3:
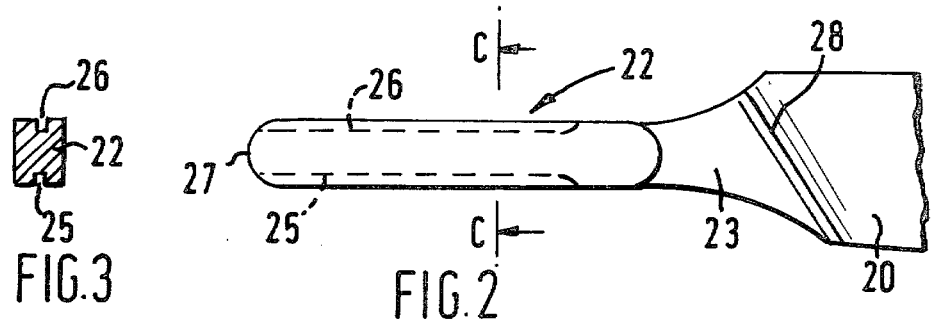
FIG. 2 is a plan view of the distal end of a scalpel handle and tang which receives the blade shown in FIG. 1.
FIG. 3 is a transverse section of the tang taken along the line C—C.
Figure 4:
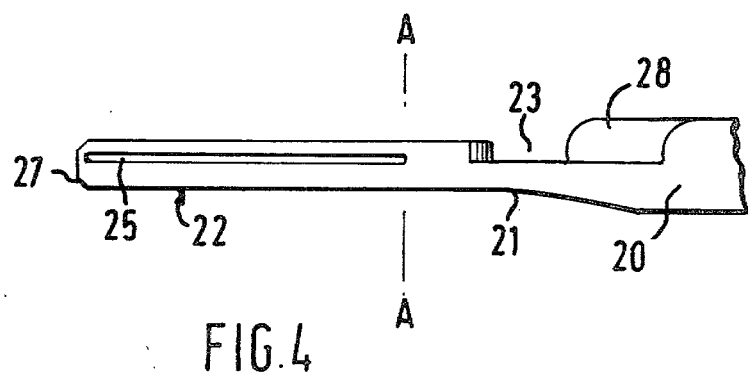
FIG. 4 is a side view of the scalpel handle and tang.

It is known to provide scalpels formed with a handle and replaceable blades. The handle can be sterilised and re-used repeatedly, and the blades are supplied in sterile packages and are discarded after use. A surgeon may use a number of scalpels during an operation, and removing the used blades from the handles is an unpleasant and hazardous task.

The construction of scalpels with removable blades is laid down by national standards organizations, the current U.K. standard being BS 2982. A handle 20 terminates in a laterally convergent intermediate region 21 which terminates in a relatively long and thin tang 22. The region 21 between the handle and the tang is cut-away to define a relieved planar face 23 which lies in the central lateral plane of the tang.

The tang is formed with opposed lateral slots 25 and 26 which extend between its distal end 27 and a transverse line A—A closely spaced from its proximal end. A disposable blade 24 is formed at its distal end 30 (only part shown) with a cutting edge 31 and fits at its proximal end to the handle 20 by engagement with the tang 22 and intermediate region 21. It is formed with a longitudinal slot having first, second and third regions 33, 34 and 35 whose width increases successively in the proximal direction. The third or proximal region 35 is sufficiently wide to clear the proximal end of the tang 22, the second or intermediate region 34 is wide enough for sliding engagement with the lateral grooves 25, 26 and the first or distal region 33 is dimensioned to receive the distal end 27 of the tang 22. The blade is fitted to the handle by bending the blade slightly, inserting the distal end 27 of the tang into the widest region 35 of the slot, advancing the blade until the intermediate region 34 locates with the grooves 25 and 26, and continuing to advance the blade longitudinally until its proximal end edge 29 registers with the boundary 28 between the handle 20 and the intermediate region 21. The blade is then allowed to straighten so that its proximal region lies flat against the relieved face 23 and the proximal end of the tang 22 protrudes through the widest region 35 of the slot so that relative longitudinal movement between the blade 24 and the handle 20 is prevented.

The way in which a blade is removed is the reverse of the way in which it is fitted. Its proximal end is levered upwardly away from contact with the relieved face 23 until the proximal end of the tang 22 can be disengaged from the proximal region 35 of the blade slot, the blade hinging about the line A—A. The blade 24 is then free to slide longitudinally off the tang 22. However, the present practice is to manipulate the blade off by means of tweezers or a forceps device which is a disagreeable and/or hazardous task.

DESCRIPTION OF PREFERRED EMBODIMENTS

A first embodiment of a hand-held blade extractor according to the inventions (FIGS. 5 and 13) has a handle 40 and a body 41. Its construction and operation will be described with the blade extractor being held so that the handle 40 is directed vertically downwards, but this orientation is adopted merely for convenient reference and the device will work equally well any way up.

The top end of the handle is cranked over to define a lower wall 46 for the body having a top face 47 over which a scalpel from which the blade is to be removed is advanced in the direction of an arrow 48. The wall 46 is formed at its distal edge with laterally opposed protuberant regions 43 and 44 whose inner edges 43a, 44a are laterally convergent and define at the extremity of wall 46 a slot 45 dimensioned to receive the tang 22 but not a blade 24. The intermediate region 21 at the end of the scalpel handle 20 is asymmetric because the boundary 28 is obliquely directed and therefore the edge 43a is cut-out to enable the handle to be advanced fully home with distal end faces of the intermediate region 21 to each side of the tang 22 positively located in contact with the respective inner edges 43a, 44a, of the protuberant regions. The blade 24 of a scalpel therefore slides over the protuberant regions 43a, 44a with the underlying portion of the tang 22 engaging the convergent proximal regions of the inner walls 43a, 44a which guide it towards the slot 45.

Lateral walls 49 and 50 of the body 41 extend upward from the lower wall 46 and support a roof 51 overlying the protuberances 43 and 44 whose proximal end terminates in a downwardly directed transverse wall 52 spaced rearwardly of the slot 45. The lower edge of the transverse wall 52 is spaced from the underlying wall 46 of the body to allow insertion of the scalpel blade and tang therebetween and supports a rearwardly directed guide wall 53 whose lower face 54 is directed at a small acute angle to the top face 47 of the wall 46. The faces 46, 54 converge in the distal direction to guide the blade 24 towards the protuberances 43 and 44 and assist in locating the tang 22 in the slot 45.

Figure 10:
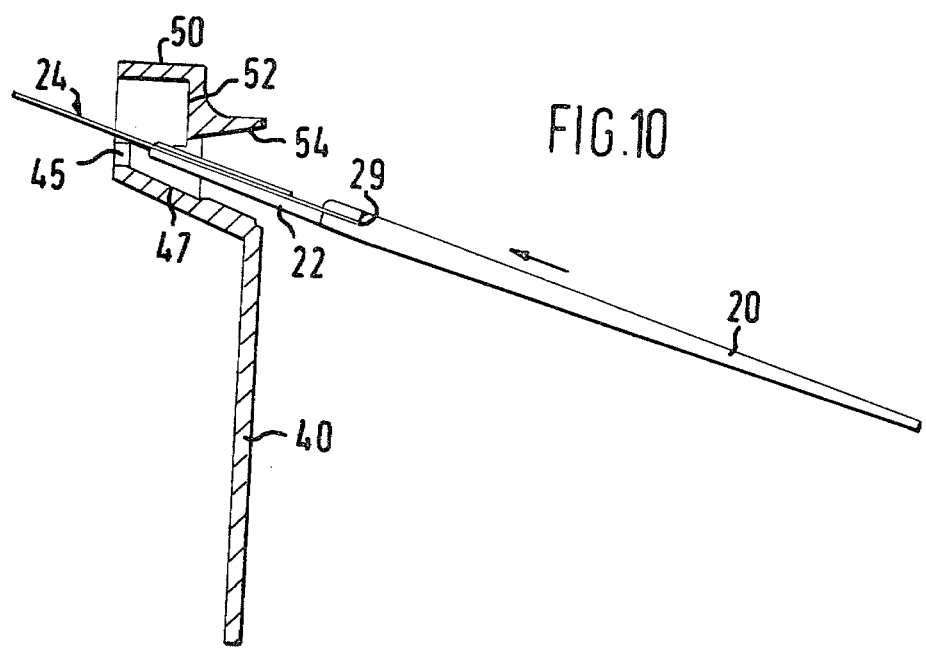
FIGS. 10 to 13 show successive stages in the removal by the blade extractor shown in FIG. 5 of a disposable blade from its handle.
Figure 11:
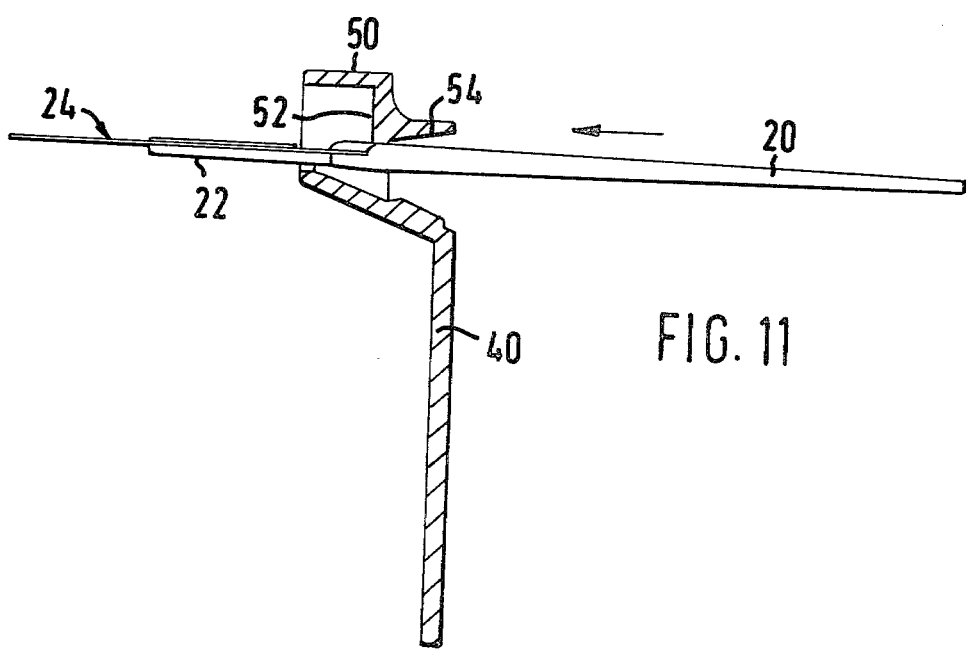
Figure 12:
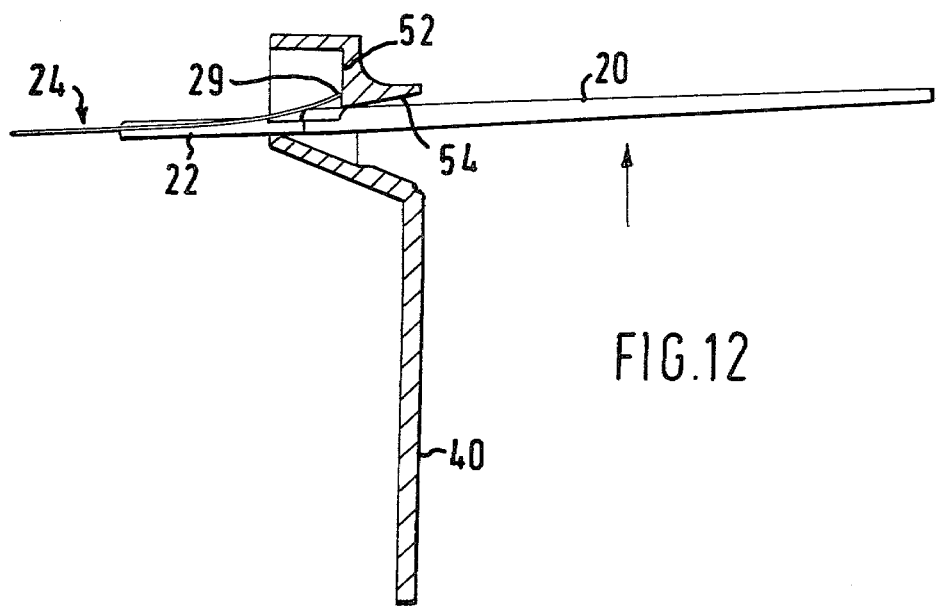
Figure 13:
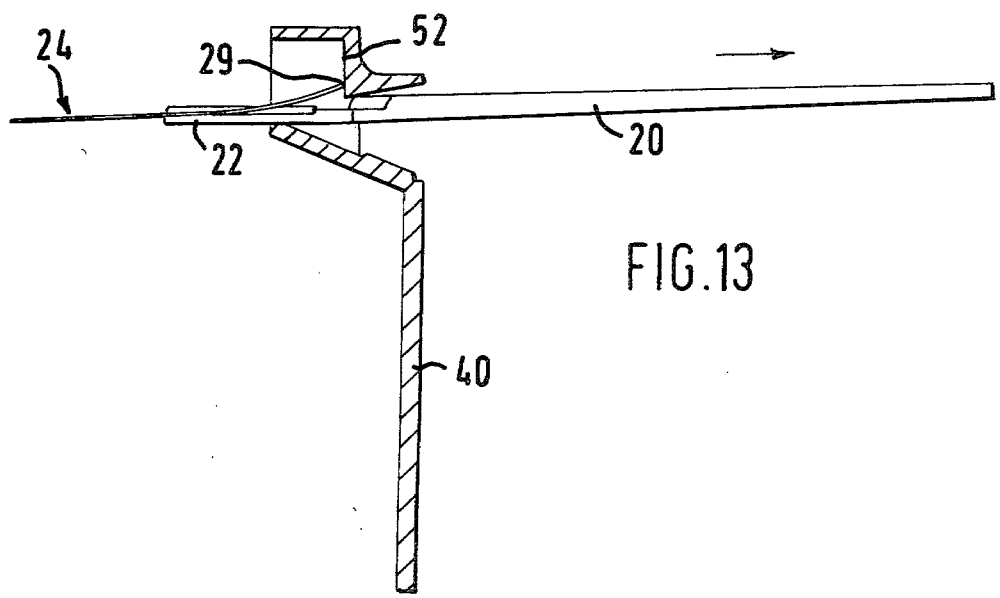

For removal of a blade, a scalpel is inserted into the device at a generally upward inclination parallel to the face 47 as shown in FIG. 10 with the tang 22 engaging the slot 45. When the intermediate region 21 has contacted the protuberant regions 43 and 44, the handle 20 of the scalpel is lifted to rotate it to the position shown in FIG. 11 in which the distal extremity of the handle 20 pivotally engages the lower end of the transverse wall 52. It will be appreciated that in this position the line A—A on the blade should be approximately level with the slot 45 and the proximal end 29 of the blade should be level with or just forwardly of the transverse wall 52. The slot 45 is deeper than the half-depth of the tang 22, so that the scalpel can be further rotated to the position shown in FIG. 12 in which the tang is urged further down into the slot 45 and the proximal end of the blade is deformed upwardly so that its proximal end 29 is retained against the transverse wall 52. The handle can then be withdrawn as shown in FIG. 13 and the blade which is prevented from moving with the handle disengages from the grooves 25 and 26 and can be removed from the tang.

A second embodiment of the blade extractor is shown in FIGS. 14 and 17 and is generally similar to the previous embodiment. However, the handle 40 has been reduced to a stub 40' which acts as a lateral and vertical finger shield and as an additional guide face for guiding the scalpel blade and tang towards the slot 45. The lower body wall 45' and lower portions 49' and 50' of the lateral body walls are extended to define a blade receiving tray 59 formed at opposed lateral edges with longitudinal recesses 60, 61 which sildably receive ribs 62, 63 of a removable cover 64 of transparent plastics material. The tray 59 and cover 64 act as a two-part closed handle for the blade extractor, into which a plurality of blades can be received. The handle can be emptied out when required by removal of the cover 64 which slides axially away from the blade extractor body 41.

The blade extractor may be made from plastics material such as ABS, polyethylene or polypropylene by injection moulding and is simple, effective and inexpensive. It will be appreciated that various modifications may be made from the embodiments described herein without departing from the invention, the scope of which is defined by the appended claims.

I claim:

1. A device for removing a detachable blade from a scalpel or the like in which a slotted blade is received in opposed lateral grooves in a thin elongate tang with a proximal region of the blade located behind the tang in a cut-away laterally convergent region intermediate the tang and the handle, the device including a base wall over whose surface the scalpel is advanced and having laterally opposed protuberant regions over which the blade slides and a slot between the protuberant regions which can receive the tang but not the blade, a fully inserted position of the scalpel being defined by abutment between the proximal edges of the protuberant regions and said convergent region, a rear wall supported behind the slot with its lower edge spaced from the base wall to allow the scalpel and blade to be inserted therebetween and to allow a fully inserted scalpel to be pivoted about the lower edge to a tilted orientation in which the proximal end of the blade is levered away from the intermediate region clear of the tang and is retained by interference with the rear wall during removal of the scalpel handle in the titled orientation, and guide surfaces proximally of the slot for directing the scalpel blade or handle into the slot.

2. A device according to claim 1, wherein a second wall extends proximally from the rear wall with its lower face directed at an acute angle thereto for guiding the blade towards the slot.

3. A device according to claim 1, wherein lateral walls extend distally from the slot to define a blade receiving tray, and a removable cover has edges slidable longitudinally into engagement with the tray to define with the tray a closed blade receiving cavity.

4. A device according to claim 3, wherein the tray and cover are shaped to provide a handle for the device.

5. A device according to claim 4, wherein the base wall is formed with lateral and downward extensions providing a guard for the handle.

* * * * *